United States Patent [19]

Macho et al.

[11] Patent Number: 5,827,477

[45] Date of Patent: Oct. 27, 1998

[54] PROCESS FOR THE PREPARATION OF A DIAGNOSTIC TEST CARRIER AND THE CARRIER THUS PRODUCED

[75] Inventors: Heinz Kurt Macho, Fürth/Fahrenbach; Klaus Dieter Hungenberg, Birkenau-Hornbach, both of Germany

[73] Assignee: Boeringer Mannheim GmbH, Mannheim, Germany

[21] Appl. No.: 6,194

[22] Filed: Jan. 19, 1993

Related U.S. Application Data

[63] Continuation-in-part of Ser. No. 205,319, Jun. 10, 1988, abandoned.

[30] Foreign Application Priority Data

Jun. 27, 1987 [DE] Germany .......................... 37 21 236.2

[51] Int. Cl.[6] .................................................. G01N 33/52
[52] U.S. Cl. .............................. 422/56; 436/170; 156/291
[58] Field of Search ........................ 422/56–58; 436/170; 156/167, 291, 295

[56] References Cited

U.S. PATENT DOCUMENTS 3,993,451  11/1976  Verbeck .

FOREIGN PATENT DOCUMENTS

| 360961 | 2/1981 | Australia . |
|---|---|---|
| 0158190 | 10/1985 | European Pat. Off. . |
| 0164960 | 12/1985 | European Pat. Off. . |
| 0166365 | 1/1986 | European Pat. Off. . |
| 0287883 | 10/1988 | European Pat. Off. . |
| 0290921 | 11/1988 | European Pat. Off. . |
| 2154737 | 9/1985 | United Kingdom . |

Primary Examiner—Jeffrey Snay
Attorney, Agent, or Firm—Fulbright & Jaworski

[57] ABSTRACT

Two absorbent layer materials for a sample liquid are connected with one another in such a way that the sample liquid can pass through from one layer into the other layer through the connecting surface between the layers a hot melt adhesive is applied to the first layer material in the form of a discontinuous coating and the second layer material is pressed on while the melt adhesive is still sufficiently hot. The amount of the melt adhesive and the pressing-on force are adjusted to one another with regard to the surface properties in such a manner that, even after the application and pressing on of the second layer material, a continuous liquid-permeable melt adhesive layer does not result. The diagnostic test carrier for the investigation of a sample liquid has two absorbent layers arranged over one another so that the sample liquid can pass through the connecting surface between the layers from one layer into the other, wherein the absorbent layers are connected with one another by a discontinuous liquid-permeable melt adhesive layer.

23 Claims, 2 Drawing Sheets

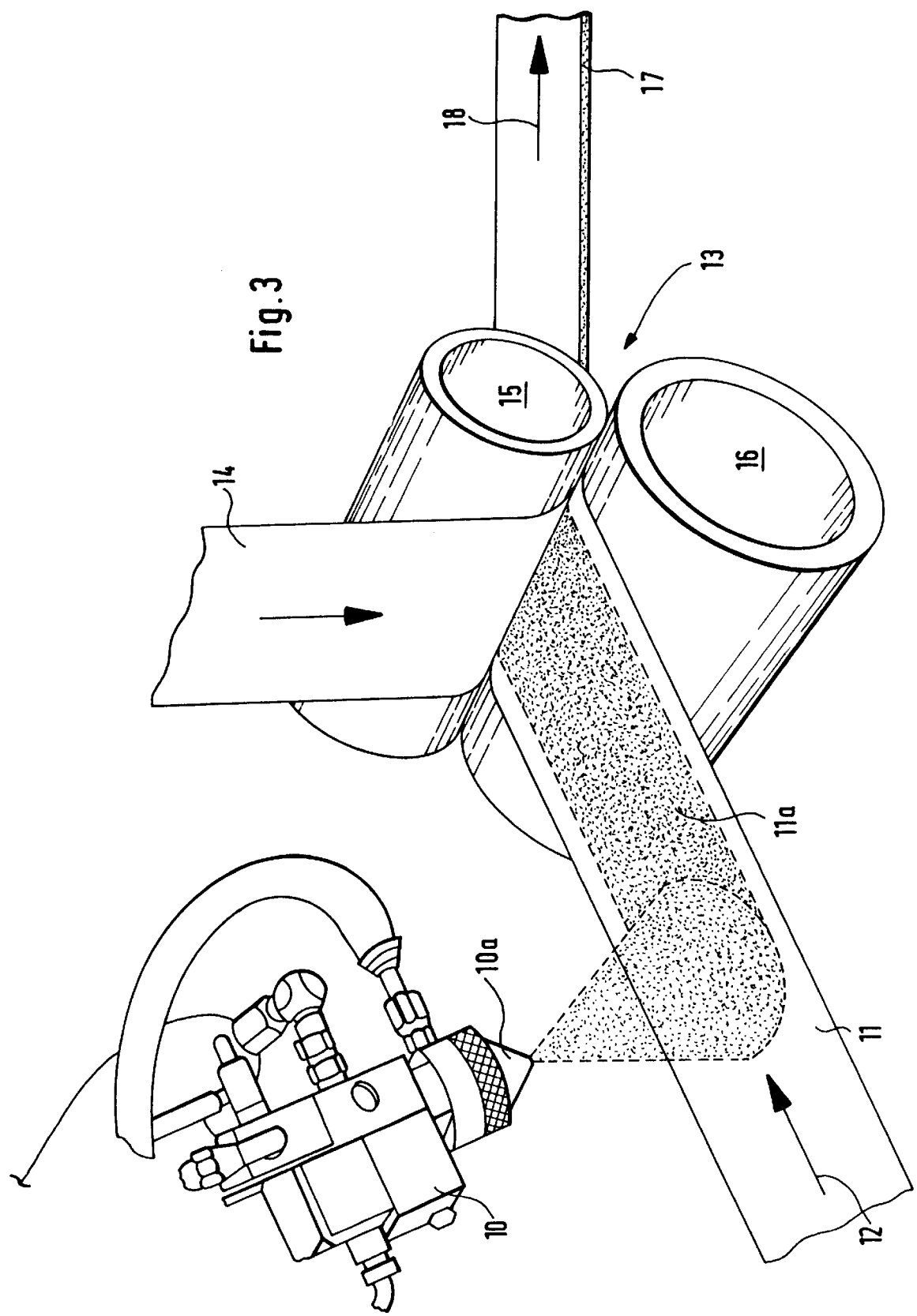

PROCESS FOR THE PREPARATION OF A DIAGNOSTIC TEST CARRIER AND THE CARRIER THUS PRODUCED

This application is a continuation-in-part of application Ser. No. 07/205,319, filed Jun. 10, 1988, now abandoned.

BACKGROUND OF THE INVENTION

The present invention is concerned with a process for the production of a diagnostic test carrier and with the test carrier thereby produced.

More particularly, the present invention is concerned with a process for the production of a diagnostic test carrier for the investigation of a sample liquid which includes a process step in which two layer materials absorbent for the sample liquid are connected together in such a manner that the sample liquid can pass through the connecting surface between the two layers from one layer into the other. The present invention also provides a corresponding test carrier.

For the qualitative or quantitative analytical determination of components of body fluids, especially of blood, so called carrier bound tests have recently been increasingly used. In these, reagents are embedded in appropriate layers of a solid test carrier which is brought into contact with the sample. The reaction of sample and reagents leads to a detectable signal, especially to a color change, which can be evaluated visually or with the help of an apparatus and usually by reflection photometry.

Tests carriers are frequently constructed as test strips which consist essentially of a longitudinal carrier layer of synthetic resin material with test layers applied thereto. However, test carriers are also known which are made as quadratic or rectangular platelets.

Known test carriers frequently contain several layers which are absorbent for the sample liquid, which term is here also to be understood to include a liquid derived from a sample. It is frequently preferred to arrange these layers over one another so that the liquid passes from one layer through the connecting surface between the two layers and penetrates into the next, adjacent layer.

Hitherto, such a layer connection of adjacent absorbent layers has only been possible to a limited extent because there are no appropriate processes for the proper assembly of the absorbent layers. This is especially true when a comparatively complicated, multi-layer construction is necessary in which the layers are produced separately and are fixed together thereafter.

In the case of urine test strips, such connections are frequently produced by bridging over several test layers together with a fine mesh which is laterally fixed on to the support material of the test strip. This manner of fixing is described, for example, in Federal Republic of Germany Patent Specification No. 21 18 455 and in the corresponding U.S. Pat. No. 3,802,842. However, it is not very suitable for the analysis of small amounts of sample such as are used, for example, in the investigation of blood.

In the case of another known process, two or more test layers are connected with the help of a laterally arranged melt adhesive strip. However, this process is only possible when it it possible to apply the melt adhesive strip, on the appropriate side. Consequently, the possibilities of use of this type of fixing are limited.

Recently, it has been suggested in European Patent Specification No. 0,208,952 now U.S. patent application Ser. No. 879,378 to stitch together several test fields arranged on top of one another. This process admittedly provides considerable improvements but results in an increase of the production costs and cannot be used in every situation.

SUMMARY OF THE INVENTION

It is an object of the present invention to provide a process and an appropriate test carrier with which, on the one hand, absorbent test carrier layers can be fixed to each other dependably and, on the other hand, economically, in such a manner that a liquid transfer through the connecting surface from one layer to another is possible. The edges of the layers are not to be used for the connection.

Thus, according to the present invention, there is provided a process for the production of a diagnostic test carrier for the investigation of a sample liquid, which comprises a process step in which two absorbent layer materials for a sample liquid are connected with one another in such a way that the sample liquid can pass through from one layer into the other layer through the connecting surface between the layers, wherein a melt adhesive is applied to the first layer material in the form of a discontinuous coating and the second layer material, while the melt adhesive is still sufficiently hot in order to retain its ability to bind, is pressed on whereby the amount of the melt adhesive and the pressing-on force are adjusted to one another with regard to the surface properties in such a manner that, even after the application and pressing on of the second layer material, a continuous liquid-impermeable melt adhesive layer does not result.

The present invention also provides a diagnostic test carrier for the investigation of a sample liquid with two absorbent layers which are arranged over one another in such a manner that the sample liquid can pass over through the connecting surface between the layers from one layer into the other, wherein the absorbent layers are connected with one another by a discontinuous, liquid-permeable melt adhesive layer.

As connecting surface in the meaning of the present invention is to be regarded the surface on which the two layers are in close vicinity with one another in such a manner that a liquid transfer from one layer into the other is possible. Of course, the layers can, in each case, be greater than the connecting surface, in which case parts of the layers then only have a loose or even no contact with one another so that, in these regions, no liquid transfer is possible.

As melt adhesives, there can be used commercially available products, for example those based upon ethylenevinyl acetate co-polymers, polyesters or polyamides. Such melt adhesives have hitherto already been used in the production of diagnostic test carriers in which case they were applied on to the whole surface of a layer to be connected and the other layer was pressed against the melt adhesive surface.

All known melt adhesive materials are not easily wetted by aqueous liquids such as typical medical sample liquids (serum or urine). This may well be an important reason why experts in the field have hitherto been put off from using a discontinuous melt adhesive layer for the connection of two absorbent test carrier layers. It was certainly the view that, in the case of small amounts of applied melt adhesive, a sufficiently dependable connection would not be obtained or that, in the case of a correspondingly increased application of melt adhesive, a dependable liquid transfer from one layer to the other would not be possible.

Surprisingly, we have found that, in the case of appropriate adjustment of the amount of melt adhesive and of the force of pressing on, having regard to the surface properties of the layers to be connected with one another, both requirements can be combined with one another. In view of the high viscosity of hot melt adhesive even by the time of its application and in view of the fast drop of temperature when small dots of hot melt adhesive are applied to a relatively large surface, the hot melt material is not easily compressed when the two layers of absorbent test layer material (such as paper, fabric, fleece or porous plastic membrane) are assembled. Therefore, the layers essentially are not in immediate contact with each other. Rather the neighboring surfaces of the layers in the adhesive-free parts of the connecting surfaces remain spaced apart from each other by a gap of capillary dimensions. Practical experiments have shown that the distance of the connected surfaces is of the order of 0.1 mm (up to 0.2 mm) and it is believed that with most standard test layer materials and available hot melt adhesives it is not possible to reduce such distance (i.e. the widths of the gap) to less than 0.05 mm or at best 0.03 mm. The precise process conditions can be ascertained on the basis of the present invention and of the instructions given hereinafter.

The application of the melt adhesive preferably takes place either by spraying on or by means of a printing technique.

Spraying on can take place with the help of a spray device which applies the heated melt adhesive and air, an entanglement of filamentary melt adhesive thereby resulting. Although this entanglement in the case of the given necessary amounts of melt adhesive achieves a considerable thickness, we have found that the liquid transfer from one layer into the other is not prevented to a degree which disturbs sample analysis. For this purpose, it is advantageous when the amount of melt adhesive applied is from 2 to 50 $g/m^2$ and preferably of from 10 to 25 $g/m^2$. The pressure force by which the two layers are pressed together preferably is in the range from 0.2 to 2.0 bar.

In the case of using a printing technique, the melt adhesive is applied to the first layer material in the form of particle or dots which are liquid-impermeable themselves but only cover the connecting surface such that between them there are present melt adhesive-free regions.

For good analytical results it is important that the surface of both layers remains even and flat even after having been connected to each other. Typical absorbent test layers are very thin (less than 0.2 mm, oftentimes less 0.1 mm) and mechanically weak. Therefore the hot melt adhesive has to be applied in relatively high density. In the case of applying the adhesive in the form of dots, at least 25 dots per $cm^2$, preferably at least 50 dots per $cm^2$ and most preferably at least 90 dots per $cm^2$ are applied. The average distance between the borders of adjacent dots should be less than 2 mm, preferably less than 1 mm and most preferably less than 0.5 mm. In the case of the spraying process, the distances of the individual filaments of the filamentary array are naturally smaller than 0.5 mm. In the context of the instant invention it has been found that even with such small distances of the hot melt particles and filaments respectively, the sample liquid penetrates evenly from the first to the second absorbent layer. The distribution per unit surface area of hot melt does not necessarily have to be uniform. Melt particles with an average surface area of at most 1.0 $mm^2$ and especially preferably of at most 0.3 $mm^2$ are preferred.

As technique for making the devices, printing or application with the help of a wheel application device are especially preferred.

BRIEF DESCRIPTION OF THE FIGURES

FIG. 3 is a perspective illustration of a spray process according to the present invention.

DETAILED DESCRIPTION OF PREFERRED EMBODIMENTS

Figure 1:
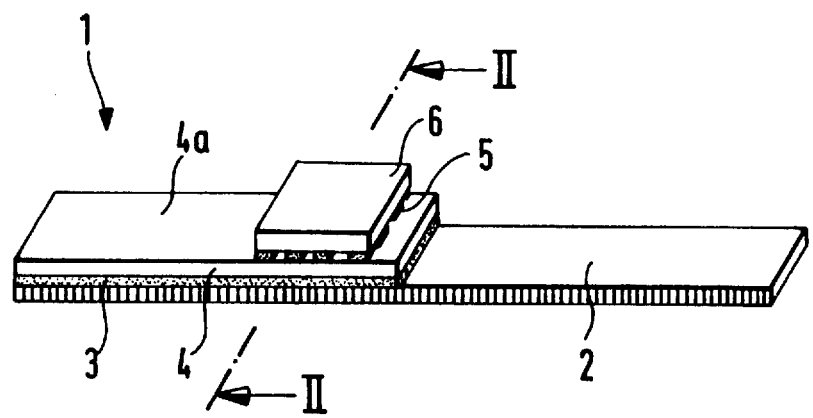
FIG. 1 is a perspective view of a test carrier according to the present invention.
Figure 2:
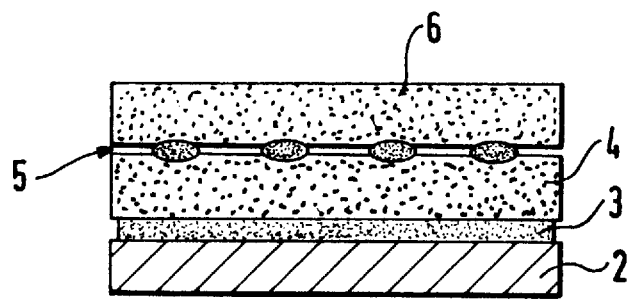
FIG. 2 is a cross-section along the line II—II in FIG. 1.

The test carrier 1 illustrated in FIGS. 1 and 2 comprises a carrier layer 2, which usually consists of a synthetic resin film. On the carrier layer 2 is fixed a first absorbent layer 4 with the help of a continuous melt adhesive layer 3.

On this in turn is fixed a second absorbent layer 6 using a discontinuous, liquid-permeable melt adhesive layer 5. The discontinuous, liquid-permeable melt adhesive layer 5 is shown considerably enlarged in the Figures in the form of comparatively large spots. In the case of application with a spray process, the layer consists of an entanglement of very thin filaments and, in the case of application with a printing technique, it consists of a very large number of very small melt adhesive particles, distributed over the connecting surface between the layers 4 and 6, which particles can be formed as round spots or also, for example, as squares or rectangles. In either embodiment (FIG. 1 or 2), the layers 4 and 6 are spaced apart by dots of hot melt adhesive 5 to form a capillary gap in the direction perpendicular to the layers.

FIG. 1 merely shows the principle of a layer construction such as can be used as construction element in various versions of test carriers. Thus, for example, the absorbent layer can be used as a transport layer on which can be applied the sample liquid in the region 4a of the layer 4 not covered by the second layer 6, the liquid being transported from there under the layer 6. In this case, the second absorbent layer 6 can be, for example, a color reaction layer in which a reaction takes place leading to a color change which can subsequently be evaluated. For this purpose, it is important that the sample liquid passes over from the layer 4 uniformly and sufficiently quickly into the layer 6, as is achieved by the present invention.

In another case, the sample can be applied directly to the layer 6, where it is distributed. In this case, an excess of sample is sucked by the first layer 4. Here, too, good liquid transfer between the layers is important.

Of course, the present invention also includes cases in which the two absorbent layers have sufficient strength in order to be used without an additional carrier layer 2. However, the illustrated construction, in which the first absorbent layer is, for its part, stuck full-facedly on a carrier is especially preferred.

In the case of the spray process illustrated in FIG. 3, the melt adhesive is sprayed with the help of a spray device 10 on to a strip of a first layer material 11 which is passed in the direction of the arrow 12 under the spray device 10 to a pressing-on device indicated as a whole by 13, the melt adhesive sprayed on forming a discontinuous coating 11a.

To the pressing-on device 13 a strip of a second layer material 14 is supplied. Rollers 15 and 16 of the pressing-on device 13 are pressed against one another with adjustable pressure. In this way, the force can be adjusted with which the two layer materials 11 and 14 are pressed together in the slot between the roller 15 and 16.

By these means, the layer materials 11 and 14 are stuck together to give the final layer connection 17 which leaves the pressing on device 13 in the direction of the arrow 18.

As mentioned hereinbefore, the spraying of melt adhesive on to a material surface to be stuck is in itself known. An appropriate spray head is, for example, commercially available from the company Meltex, Luneberg, Federal Republic of Germany. Therefore, it is not necessary to describe the spray device 10 in detail.

However, it is important that the process parameters, in the case of the spraying, are so adjusted that clean application to the first layer material is achieved. It is preferred to work with a relatively low air pressure, preferably of less than 1 bar. The spray nozzle 10*a* should preferably be arranged vertically to the strip of the first layer material 11.

As mentioned above, the amount of melt adhesion layer 11*a* sprayed on and the pressing-on force of the pressing-on device 13 are chosen having taken into consideration the surface properties of the layer materials 11 and 14 to be connected together. Thus, the amount of melt adhesion and pressure force are so adjusted with regard to one another that a liquid-permeable, continuous layer of melt adhesive is not formed after the pressing on of the second layer material. Orienting statements within which ranges these parameters preferably vary have been made hereinbefore. On this basis, the individual cases can be optimized.

The application temperature of the melt adhesive and the cooling thereof up to the point of time of the pressing together are thereby also to be taken into account. This is determined by the speed of transport of the first layer material and the distance of the application device 10 from the pressing-on device 13. The more the melt adhesive cools, the less is the danger during the pressing on of the second layer 14, that the adhesive spreads and prevents passage of liquid through the melt adhesive layer. On the other hand, however, it must still be sufficiently hot in order to ensure dependable adhesion.

Instead of the spray process illustrated in FIG. 2, as mentioned above, a wheel application device or a screen printing device can also be used, in order to apply the discontinuous coating to the first layer material.

A wheel application device operates with a roller-like application wheel which rotates in a container in which is present the molten melt adhesive. The roller surface has engraved-in depressions, the shape and distribution of which on the roller surface correspond to the desired melt adhesive regions. In the case of rotation of the wheel through the melt adhesive, this is taken up in the depressions. An excess is removed by a doctor blade and the adhesive melt regions are transferred from the application wheel to the absorbent layer material.

Since the wheel application of melt adhesive is itself known, it is here not necessary to give more details. Considerations as employed in using spray application means apply here as well.

Screen printing devices for the application of the melt adhesives are also known. They operate with a perforated roller through the openings of which the melt adhesive can be applied to a strip of material passing in under the roller. Process parameters, as discussed supra, also apply here.

The following Examples are given for the purpose of illustrating the present invention.

EXAMPLE 1

A test carrier with the construction illustrated in FIG. 1 is produced with the use of the following materials:
carrier layer 2: Hostaphan RN 350 of Kalle AG, Federal Republic of Germany
melt adhesive
for layers 3 and 5: EVA (ethylene vinyl acetate) melt adhesive "Jet-Melt 3764" of the 3M Company
first absorbent
layer: fibre fleece VLS 3512 with a thickness of 0.33 mm; Schleicher & Schüll, Federal Republic of Germany
second absorbent
layer 6: reaction layer based on a monofilar or multifilar polyester fabric impregnated with reagents for the determination of protein, pH and blood in urine, as well as of sugar in blood, with a thickness of 0.4 mm.

The application of the discontinuous melt adhesive layer 5 takes place with a melt adhesive spray application head "Meltex EP 25S", with the maintenance of the following conditions:
application temperature of the melt adhesive spray application: 170° C.
distance of the spray nozzle 10/pressing-on device 13; 180 mm
distance of spray nozzle 10/first layer material 11: 25 mm
pressing-on force of the rollers 15, 16 against one another: 1.0 bar
air pressure of the spray head: 0.2 bar
band speed: 155 m/min.
amount of adhesive in the case of the spray application: about 20 g/m$^2$ With these process conditions, there was achieved a dependable connection between the layers 4 and 6, independent of the reagent impregnation of the layer 6. At the same time, there was obtained an excellent liquid transfer between the layers. This applied to both the following applications:
in the case of a blood determination, the sample was applied to the layer 4 in the region 4*a* and from there transported under the layer 6 and absorbed by this;
in the case of a urine test, the sample was applied directly to the layer 6 and the layer 4 served as an absorbing layer for absorbing excess of the sample.

EXAMPLE 2

A test carrier with the construction illustrated in FIG. 1 was produced completely analogously to Example 1. However, the absorbent layer 6 consisted of a fibre fleece or of paper with a thickness of 0.4 mm. With this there were obtained substantially the same results as previously described in Example 1.

EXAMPLE 3

A similar test carrier construction was produced with a wheel application device. The wheel was thereby engraved with depressions of 0.1 mm depth, the surface of which, in each case, was about 0.1 mm$^2$, a total of 20% of the connecting surface thereby being coated with melt adhesive.
Process parameters:
melt adhesive application temperature: 150° C.
pressing-on roller heated to: 40° C.
pressing-on force: 1 bar
In this case, too similarly good results were obtained as with the spray application.

It will be understood that the specification and examples are illustrative but not limitative of the present invention and that other embodiments within the spirit and scope of the invention will suggest themselves to those skilled in the art.

We claim:
1. Test carrier for analysis of a liquid sample, said test carrier comprising
   a first absorbent layer having a surface,
   a second absorbent layer having a surface facing said surface of said first absorbent layer, and an array of dots of hot melt adhesive connecting said surfaces of said first and second layers, said array comprising at least 25 dots per cm$^2$, wherein said dots of hot melt adhesive have a dimension perpendicular to said surfaces which keeps said surfaces spaced apart by a gap of 0.05 to 0.2 mm, said dots and said cap being dimensioned such that a liquid sample can pass from said surface of said first absorbent layer to said surface of said second absorbent layer.

2. Test carrier as in claim 1 wherein said array comprises at least 50 dots/cm$^2$.

3. Test carrier as in claim 2 wherein said array comprises at least 90 dots/cm$^2$.

4. Test carrier as in claim 1 wherein said dots cover at least 50% of the surface of each layer.

5. Test carrier as in claim 1 wherein each dot covers a maximum of 1.0 mm$^2$ of the surface of each layer.

6. Test carrier as in claim 5 wherein each dot covers a maximum of 0.3 mm$^2$ of the surface of each layer.

7. Test carrier for the analysis of a liquid sample, said test carrier comprising a first absorbent layer having a surface, a second absorbent layer having a surface facing said surface of said first absorbent layer, a filamentary array of hot melt adhesive connecting said surfaces of said first and second layers, said array having a dimension perpendicular to said surfaces which keeps said surfaces spaced apart by a gap of 0.05 to 0.2 mm.

8. Method of manufacturing a test carrier for analysis of a liquid sample, said method comprising providing a first absorbent layer having a surface and a second absorbent layer having a surface, applying hot melt adhesive to the surface of said first layer in an array of dots comprising at least 25 dots/cm$^2$, and applying said surface of said second layer against said array so that said surfaces are spaced apart by a gap of 0.05 to 0.2 mm.

9. Method as in claim 8 wherein said array comprises at least 50 dots/cm$^2$.

10. Method as in claim 9 wherein said array comprises at least 90 dots/cm$^2$.

11. Method as in claim 8 wherein said surface of said second layer is applied so that said dots cover at least 50% of the surface of each layer.

12. Method as in claim 8 wherein said second layer is applied so that each dot covers a maximum of 1.0 mm of the surface of each layer.

13. Method as in claim 12 wherein said second layer is applied so that each dot covers a maximum of 0.3 mm$^2$ of the surface of each layer.

14. Method as in claim 8 wherein said hot melt adhesive is applied to said first layer in an amount ranging from 2 to 50 g per m$^2$ of said surface of said first layer.

15. Method as in claim 14 wherein said hot melt adhesive is applied to said first layer in an amount ranging from 10 to 20 g per m$^2$ of said surface of said first layer.

16. Method as in claim 8 wherein said hot melt adhesive is applied with a screen printing process.

17. Method as in claim 8 wherein said hot melt adhesive is applied with a wheel application device.

18. Method of manufacturing a test carrier for analysis of a liquid sample, said method comprising providing a first absorbent layer having a surface and a second absorbent layer having a surface, applying hot melt adhesive to the surface of said first layer by a pressurized gas spray to form a filamentary array of adhesive, and applying said surface of said second layer against said array so that said surfaces are spaced apart by a gap of capillary dimensions.

19. Method as in claim 18 wherein said hot melt adhesive is applied to said first layer in an amount ranging from 2 to 50 g per m$^2$ of said surface of said first layer.

20. Method as in claim 19 wherein said hot melt adhesive is applied to said first layer in an amount ranging from 10 to 20 g per m$^2$ of said surface of said first layer.

21. Method as in claim 18 wherein said hot melt adhesive is applied at a gas pressure in the range of 0.2 to 10 bar.

22. Method as in claim 21 wherein said pressure is in the range of 0.2 to 2.0 bar.

23. Method as in claim 18 wherein said second layer is applied against said array of melt adhesive at a pressure of 0.2 to 2.0 bar.

\* \* \* \* \*

UNITED STATES PATENT AND TRADEMARK OFFICE
CERTIFICATE OF CORRECTION

PATENT NO. : 5,827,477
DATED : October 27, 1998
INVENTOR(S) : Heinz Kurt Macho, et. al.

It is certified that error appears in the above-identified patent and that said Letters Patent is hereby corrected as shown below:

On the cover, in the section titled References Cited, Foreign Patent Documents, line 1, change "Australia" to -- Austria --.

On the cover, in the Abstract, line 4, between "layers" and "hot", delete "a" and insert therefor -- . A --.

On the cover, in the Abstract, line 7, after "hot" insert -- to be bindable --.

In column 1, line 62, after "strip" delete -- , --.

In column 4, line 42, change "sucked" to -- absorbed --.

In column 6, line 56, after "too" insert -- , --.

In Claim 1, column 7, line 6, change "cap" to -- gap --.
In Claim 12, column 8, line 5, change "1.0 mm" to --1.0 mm$^2$ Signed and Sealed this Fourth Day of April, 2000

Attest:

Q. TODD DICKINSON

Attesting Officer

Director of Patents and Trademarks